US009312111B2

(12) United States Patent
Bendall et al.

(10) Patent No.: US 9,312,111 B2
(45) Date of Patent: Apr. 12, 2016

(54) APPARATUS AND METHOD FOR SUB-MICROMETER ELEMENTAL IMAGE ANALYSIS BY MASS SPECTROMETRY

(71) Applicant: The Board of Trustees of the Leland Stanford Junior University, Stanford, CA (US)

(72) Inventors: Sean C. Bendall, San Mateo, CA (US); Robert M. Angelo, San Francisco, CA (US); Garry P. Nolan, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/673,279

(22) Filed: Mar. 30, 2015

(65) Prior Publication Data

US 2015/0287578 A1 Oct. 8, 2015

Related U.S. Application Data

(60) Provisional application No. 61/974,351, filed on Apr. 2, 2014.

(51) Int. Cl.
*H01J 49/40* (2006.01)
*G01N 33/68* (2006.01)
(Continued)

(52) U.S. Cl.
CPC ......... *H01J 49/0036* (2013.01); *H01J 49/0004* (2013.01); *H01J 49/0413* (2013.01); *H01J 49/142* (2013.01); *H01J 49/40* (2013.01); *H01J 49/401* (2013.01)

(58) Field of Classification Search
CPC . H01J 49/142; H01J 49/0004; H01J 49/0031; H01J 49/0036; H01J 49/004; H01J 49/26; H01J 49/0027; H01J 49/10; H01J 49/401; H01J 49/421; G01N 23/2258; G01N 23/225; G01N 23/2255; G01N 23/22
USPC ................. 250/282, 287, 288, 281, 307, 309, 250/423 R, 305, 306, 397, 398, 492.3
See application file for complete search history.

(56) References Cited

U.S. PATENT DOCUMENTS 4,442,354 A * 4/1984 Hurst ..................... G01N 21/63 204/192.1
4,864,130 A * 9/1989 Gruen ................... H01J 49/161 250/305
(Continued)

FOREIGN PATENT DOCUMENTS

| | | |
|---|---|---|
| WO | 0068434 | 11/2000 |
| WO | 2009156725 | 12/2009 |
| WO | 2012003478 | 10/2012 |

OTHER PUBLICATIONS

Angelo, et al., "Multiplexed ion beam imaging of human breast tumors", Nat. Med. (Apr. 2014), 20(4): 436-42.
(Continued)

*Primary Examiner* — David A Vanore
(74) *Attorney, Agent, or Firm* — James S. Keddie; Bozicevic, Field & Francis LLP

(57) ABSTRACT

A mass spectrometer system having: a primary ion source capable of irradiating a segment on a planar sample with a beam of primary ions, an orthogonal ion mass-to-charge ratio, the analyzer being configured to separate secondary elemental atomic ions according to their mass-to-charge ratio by time of flight; an ion detector for detecting secondary elemental atomic ions and producing mass spectra measurements; and a synchronizer. In the system, the beam of primary ions scans across the planar sample in two dimensions and the synchronizer associates the mass spectra measurements with positions on the planar sample.

20 Claims, 4 Drawing Sheets

(51) Int. Cl.

| | |
|---|---|
| ***H01J 49/00*** | (2006.01) |
| ***H01J 49/04*** | (2006.01) |
| ***H01J 49/14*** | (2006.01) |

(56) References Cited

U.S. PATENT DOCUMENTS

| | | | | |
|---|---|---|---|---|
| 4,912,327 | A * | 3/1990 | Waugh | H01J 27/02 250/287 |
| 5,087,815 | A * | 2/1992 | Schultz | H01J 49/48 250/287 |
| 6,291,820 | B1 * | 9/2001 | Hamza | G01N 23/22 250/282 |
| 6,534,764 | B1 | 3/2003 | Verentchikov et al. | |
| 6,627,877 | B1 | 9/2003 | Davis et al. | |
| 6,777,671 | B2 * | 8/2004 | Doroshenko | H01J 49/004 250/281 |
| 6,833,544 | B1 * | 12/2004 | Campbell | H01J 49/4225 250/281 |
| 6,849,848 | B2 | 2/2005 | Baranov et al. | |
| 6,989,528 | B2 * | 1/2006 | Schultz | H01J 49/0031 250/281 |
| 7,170,052 | B2 * | 1/2007 | Furutani | B82Y 10/00 250/281 |
| 7,700,295 | B2 | 4/2010 | Baranov et al. | |
| 7,728,287 | B2 | 6/2010 | Felton et al. | |
| 7,795,579 | B2 * | 9/2010 | Komatsu | H01J 49/145 250/282 |
| 8,119,982 | B2 * | 2/2012 | Kajihara | G01N 33/6848 250/281 |
| 8,421,005 | B2 * | 4/2013 | Musselman | G01J 23/2255 250/281 |
| 8,829,428 | B2 * | 9/2014 | Schultz | G01N 23/2258 250/281 |
| 9,006,720 | B2 * | 4/2015 | Chiruvolu | B82Y 30/00 257/40 |
| 9,190,256 | B2 * | 11/2015 | Brown | H01J 49/164 |
| 2003/0008404 | A1 * | 1/2003 | Tomita | G01N 23/203 436/72 |
| 2003/0073145 | A1 * | 4/2003 | Caprioli | G01N 33/6848 435/7.23 |
| 2007/0029473 | A1 * | 2/2007 | Verentchikov | H01J 49/406 250/281 |
| 2007/0178607 | A1 | 8/2007 | Prober et al. | |
| 2008/0113875 | A1 | 5/2008 | Chaurand et al. | |
| 2008/0277576 | A1 * | 11/2008 | Komatsu | H01J 49/142 250/287 |
| 2009/0179149 | A1 | 7/2009 | Sugiyama et al. | |
| 2010/0090101 | A1 * | 4/2010 | Schultz | H01J 49/0418 250/282 |
| 2010/0144056 | A1 | 6/2010 | Winnik et al. | |
| 2010/0255602 | A1 | 10/2010 | Felton et al. | |
| 2012/0061561 | A1 * | 3/2012 | Antonov | H01J 49/0036 250/282 |
| 2012/0061564 | A1 * | 3/2012 | Tona | G01N 23/2255 250/307 |
| 2012/0077714 | A1 | 3/2012 | Nolan et al. | |
| 2012/0305758 | A1 * | 12/2012 | Park | H01J 49/063 250/282 |
| 2013/0092831 | A1 * | 4/2013 | Kyogaku | H01J 49/00 250/282 |
| 2013/0122516 | A1 | 5/2013 | Hong et al. | |
| 2014/0191123 | A1 * | 7/2014 | Wildgoose | H01J 49/061 250/282 |
| 2015/0115148 | A1 * | 4/2015 | Aoki | H01J 49/0004 250/282 |
| 2015/0155132 | A1 * | 6/2015 | Aoki | H01J 49/0004 250/306 |
| 2015/0206732 | A1 * | 7/2015 | Sakai | H01J 49/161 378/64 |
| 2015/0287578 | A1 * | 10/2015 | Bendall | H01J 49/0004 250/282 |

OTHER PUBLICATIONS

Guerquin-Kern et al., "Progress in analytical imaging of the cell by dynamic secondary ion mass spectrometry (SIMS microscopy).", Biochim Biphys Acta. (Aug. 2005), 1724(3):228-38.

Lanni, et al. "Mass spectrometry imaging and profiling of single cells", J Proteomics (Aug. 2012), 75(16):5036-51.

* cited by examiner

APPARATUS AND METHOD FOR SUB-MICROMETER ELEMENTAL IMAGE ANALYSIS BY MASS SPECTROMETRY

GOVERNMENT RIGHTS

This invention was made with Government support under contract nos. CA034233, AI057229, CA130826, EY018228, CA118681, HHSN272200700038C, and 1K99 GM104148-01 awarded by the National Institutes of Health. The Government has certain rights in the invention.

BACKGROUND

A planar sample can be analyzed by ablated the sample using a laser and then characterizing the ablated products using an ICP-MS (inductively coupled plasma mass spectrometer). The identities and the amounts of the elements associated with the sample can be stored and analyzed. The value of these laser ablation methods is limited for multiple reasons, e.g.: 1) there is a physical limitation (dictated by wavelength) on the size of the ablated segment when a laser is used for sampling, 2) the ablation is typically destructive, vaporizing the full thickness of a sample, thus preventing re-analysis, and 3) ablation and ionization of reporter elements at atmospheric pressure has reduced sensitivity from poor ion introduction into the vacuum of a mass spectrometer.

SUMMARY

This disclosure provides systems, methods, devices, and computer programming useful for, among other purposes, sub-micron sampling and ionization from a biological matrix in a vacuum with a primary ion beam and operating a mass spectrometer to measure and quantify the elemental isotopic constituents of each sampled segment. The described system and methods operate can operate with a mass analyzer that provides for temporal separation of charged particles within a flow of charged particles, based on mass and/or mass-charge ratio. The analyzed matrix includes, for example, biological tissue slices or cells that contain elemental information, or elementally-coded two dimensional standards. However, the invention is relevant to the analysis of any kind of two-dimensional substrate using a primary ion beam for vacuum-based sampling and ionization and pulsed secondary ion optics for elemental mass analysis and quantification.

For example, some embodiments provide methods and means for operating a detection system for mass spectrometry of individual sample segments by a time-of-flight (TOP) mass spectrometer (MS). In particular, this disclosure provides methods for performing multiple TOF-MS scans on a continuous introduction of elemental ions from continuously analyzed two dimensional sample segments while registering the corresponding mass information with the sample segment from which it was generated. The data can be sampled in one or more mass spectra sampling cycles as appropriate for a desired application. Sub-micrometer segments of the two dimensional analyte matrix are samples for their elemental ions using a primary ion beam or charged particle beam. Application of the beam to a particular segment of the analyte results in the secondary ionization of the elemental constituents therein.

The time window that is sampled in each single TOP-MS spectrum can correspond to the time window in which the ions of a particular staining elemental isotope, present in the sample matrix being characterized, can produce a signal at the TOF-MS detector. Simultaneously, the detection of other stained or endogenous elemental reporters falling in the other time window(s) can be achieved in the same single mass spectrum. "Staining" of the tissues can be achieved by any method consistent with the processes and objectives disclosed herein, including for example (U.S. provisional application Ser. No. 61/970,803, filed on Mar. 26, 2014, U.S. provisional application Ser. No. 61/877,733, filed on Sep. 13, 2013 and Angelo et al. Nature Medicine, published online on Mar. 2, 2014, which are all incorporated by reference herein). The series of single TOF-MS spectra can be synchronized to the dwell time of the continuous primary ion beam on each segment where all spectra for a given segment will be integrated. The integration time and number of spectra corresponding to each segment will be dynamic and dependent on the desired application.

In some embodiments, the signal that indicates the presence of an elemental reporter in an analyzed sample segment in the mass spectrometer's main ion detector that provides mass resolved data. In such case, the system can comprise one or more auxiliary detectors and this signal can be induced by ions, photons or electrons produced by the ion source, or by a neutral component of the particle which survived through the ion source in un-ionized state.

In some embodiments, the time window that is sampled in each single mass spectrum contains all mass-to-charge ratio channels of the ions of interest, including the ions of staining elements. All data from the time window is transferred and processed for each single mass spectrum where processing, including for each mass-to-charge ratio, ion counting, or summing of all signals within the pre-selected time window corresponding to a particular mass-to-charge ratio, is performed. The resulting data contains, for each single mass spectrum, a plurality of single integral values of signal strength for each mass-to-charge ratio. For a given segment of the analyzed sample, the successive integral information from each single mass spectrum are further combined based on the number of single MS scans that corresponded to the dwell time of the ion source on that segment.

In another embodiment, the time window which is sampled in each single mass spectrum, contains all expected times of arrival of the ions of interest (i.e., ail mass-to-charge ratio channels of interest), including the ions of staining elements. However, only the data from the primary mass-to-charge ratio channels, which can be referred to as a primary detection group anticipated in the sample, are transferred for further processing. As a result, the amount of data that is always processed can be kept tow.

Some embodiments provide a mass spectrometer for elemental analysis of individual sample segments, which comprises means to introduce a planar section of analyte into the vacuum of the mass spectrometer, and ionization source from which ions of individual segments with sub-micron cross-sections can be transferred into the mass spectrometer, amass analyzer to separate the ions according to their mass-to-charge ratio, an ion detector to detect the mass-to-charge separated ions, a digitizing system to digitize the output of the ion detector, means to transfer, process and record the data, means to associate the information from mass spectrometer with a given segment of the sample, and a means to synchronize at least one of the ionization system, ion detector, the digitizing system, or, the transfer, processing and recording of the data such that the mass information can be associated with each segment of the analyzed sample.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
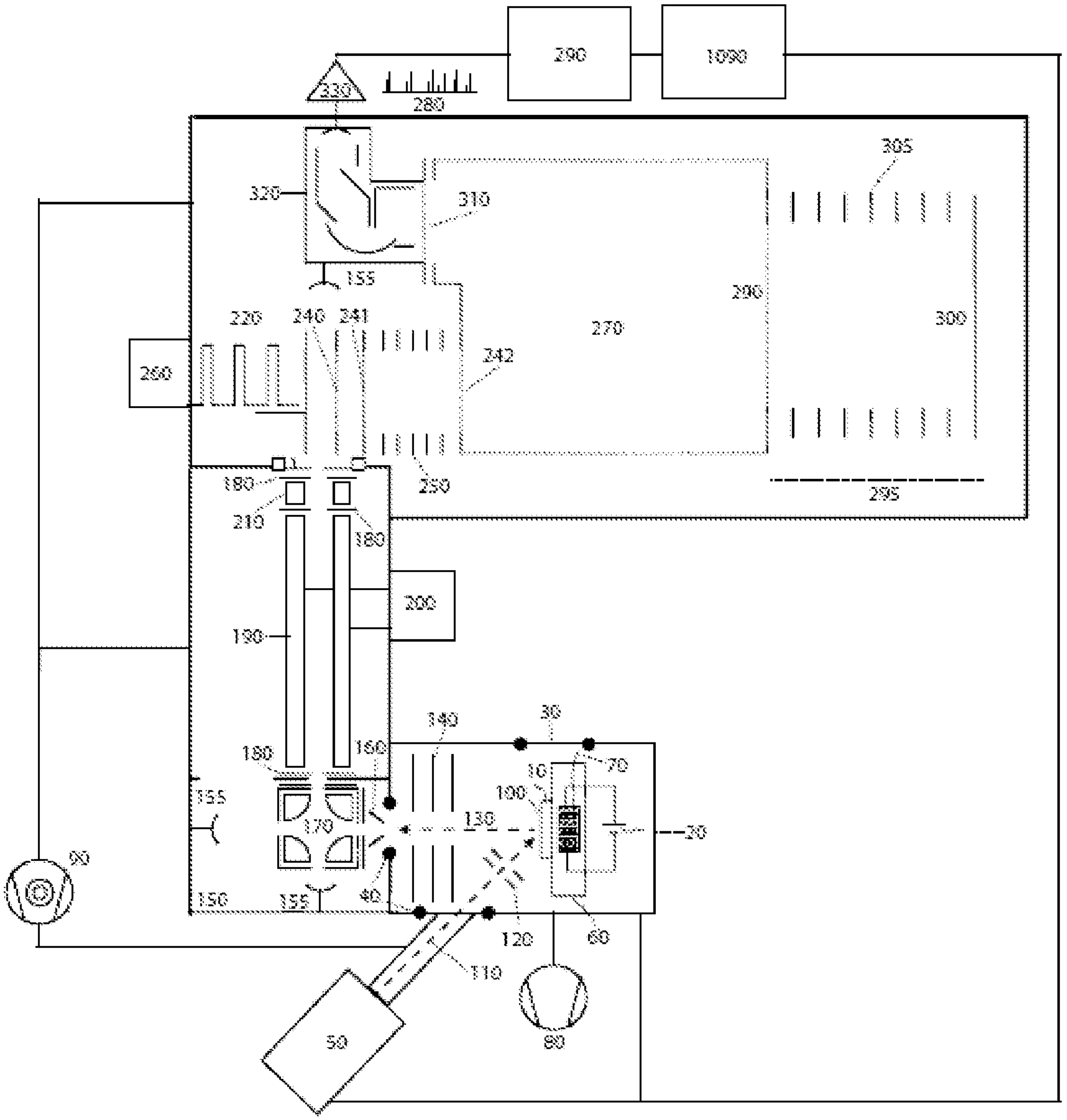
FIG. 1. A schematic illustrating an exemplary embodiment of a of a time-of-flight mass spectrometry apparatus from measuring secondary ions from a planar sample irradiated by a primary ion source in accordance with the invention described in greater detail below.

Before describing exemplary embodiments in greater detail, the following definitions are set forth to illustrate and define the meaning and scope of the terms used in the description.

As used herein, the term "planar sample" is used to refer to a substantially planar, i.e., flat, biological sample. Examples of such samples include tissue sections (e.g., sectioned using a microtome), samples that are made by depositing disassociated cells onto a planar surface, and samples that are made by growing a sheet of cells (e.g., monolayer) on a planar surface.

As used herein, the term "staining element" refers to any atomic element or isotope present in the particle or biological cell that can be analyzed by the disclosed apparatus and method. The element can be naturally present in the samples or can be an element that is purposely added to the planar matrix. For example, some cells may be abundant in Zn or Fe. Alternatively, a staining element can be specifically added (or tagged) into the sample, by any method consistent with the disclosure herein, including but not limited to using a metalointercalator to label the DNA or permeated into the cell or added by an element-tagged antibody.

As used herein, the term "mass tagged" refers to a molecule that is tagged with either a single kind of stable isotope that is identifiable by its unique mass or mass profile or a combination of the same, where the combination of stable isotopes provides an identifier. Combinations of stable isotopes permit channel compression and/or barcoding. Examples of elements that are identifiable by their mass include noble metals and lanthanide, although other elements may be employed. An element may exist as one or more isotopes, and this term also includes isotopes of positively and negatively metals. The terms "mass tagged" and "elementally tagged" may be used interchangeably herein.

As used herein, the term "mass tag" means any isotope of any element, including transition metals, post transition metals, halides, noble metal or lanthanide, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type). In some embodiments, the mass tag may have a mass in the range of 12-238 atomic mass units, e.g., 21 to 238 atomic mass units, including C, O, N and F adducts. In some embodiments, the mass tag may be an atom of an element having an atomic number in the range of 21-90, e.g., an element having an atomic number of 21-29, 39-47, 57-79 or 89. In some cases, the element is a lanthanide. In particular embodiments, labeling may be done using a specific binding reagent, e.g., an antibody that contains a chelated atom that functions as the mass tag, methods for making which are known.

As used herein, the term "mass spectrum" includes data, including raw data (e.g., a waveform) or processed data associated with the waveform, that are collected in a single sampling cycle for example after a single ion beam modulation event is applied in a mass spectrometer (such as an exemplary time-of-flight apparatus described below). For example a packet of ions in the acceleration region pushed by appropriately arranged electrical pulses into the flight tube. This can also be referred to as single sampling cycle mass spectra. Time-of-flight cycle is the period between consecutive single ion beam modulation events. Mass spectra measurements may contain the identities and abundance of mass tags that are part of the staining elements used.

As used herein, the term "ion detector" refers to any or all devices capable of collecting one or more mass spectra, or of collecting signals induced by a staining element.

As used herein, the term "data generation rate" refers to the rate at which the digitized representation of a single mass spectrum is produced. For example, if a waveform representing a single mass spectrum is of the duration of 10 microseconds, and its features require sampling of the waveform with accuracy of $10^{-2}$% in time and 0.4% signal strength, the waveform should be sampled every 1 nanosecond and with 250 levels of signal strength, resulting in approximately 10000×8 bit=10 kilobyte (kB) of data in 10 microsecond, or 1 gigabyte (GB) per second data generation rate. The Data transfer rate is the rate at which a digitized representation of a single waveform can be transferred into a memory storage device for further processing, including for example compression or recording. Spectrum generation frequency is the frequency at which consecutive single mass spectra are generated.

As used herein, the term "sample segment" or "area" is any discrete location of a planar sample suitable for mass analysis by a mass spectrometer. For example, a 0.1 um by 0.1 um section of a sample that is ionized by an ion beam for elemental mass analysis. Once digitized the composition of elemental reporters could be displayed as colors of that individual image pixel.

As used herein, the term "orthogonal" is intended to refer to a direction that is approximately 90 degrees. Specifically, in an "orthogonal" time of flight mass spectrometer, the ions change direction by about 90 degrees, relative to their prior flight path, as they enter the flight tube. In certain cases, a beam of ions may be shaped into a ribbon, e.g., using an ion slicer, and packets of ions are forced to change direction into the time of flight tube using, e.g., a pulser.

As used herein, the term "continuously irradiates" is intended to refer to a primary ion source that is substantially "on" and irradiating a sample without any interruptions. As will be discussed below, a primary ion source may continuously irradiate a sample while the beam itself is being steered across the sample (e.g., by moving the sample, by moving the ion source, or using ion optics, i.e., electrodes). A beam is substantially "on" if it has a duty cycle of at least 10%.

Unless otherwise stipulated, the term "moves" as used herein is a relative term. In "moving" an ion beam across a sample, the source of the beam can move relative to the sample, the sample can move relative to the source of the beam, or the direction of the beam can be manipulated by ion optics.

As used herein, the term "scans across the planar sample in two dimensions" is intended to mean that a beam goes back and forth in a series of substantially parallel lines across an area of a sample. "Rastering" is a type of such scanning. The spacing between the lines may vary, as may the speed at which the beam travels.

As used herein, the term "in the plane of the planar sample" is intended to refer to the x-y plane of a planar sample, where z is above or below the planar sample.

As used herein, the term "timing of the scans" is intended to an absolute (e.g., a time of day) or absolute (e.g., when one scan is done relative to another scan) indication of timing. In some embodiments, the timing of scan may be indicated by associating a scan with the resolution of a scan, e.g., if the high resolution scans happen after lower resolution scans.

As used herein, the term "position on the planar sample" may be described any suitable way, e.g., using x-y coordinates, or by a time, where the time can be used to determine the x-y coordinates of a position of the planar sample.

In any embodiment, data can be forwarded to a "remote location", where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

As used herein, the term "receiving" is used to refer the delivery of information from the memory of a computer system to a user, usually in human readable form, e.g., in the form of a figure or a text file. This term is intended to encompass delivery of an image to the screen of a computer monitor, as well as delivery of a file to a user by electronic means, e.g., by email or the like.

DETAILED DESCRIPTION

The description that follows, and the embodiments described herein, is provided by way of illustration of examples of particular embodiments of the principles of the present invention. These examples are provided for the purposes of explanation, and not limitation, of those principles and of the invention.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

A description of such embodiments may be provided by using the example of a Time-of-Flight Mass Spectrometer schematically shown in FIG. 1. FIG. 1 shows an example of a schematic of a mass spectrometry-based secondary ion imaging device suitable for use in implementing various aspects of the invention. A sample 10, which can, for example, comprise a microtome histological tissue section mounted on a substrate, for example a semiconductor wafer or conductive glass slide, is introduced into the sample interface vacuum chamber 20 through a chamber access gate 30. In order to reduce signal background arising from elemental contamination present in the substrate on which the sample is mounted, one embodiment of this substrate would be depleted of elemental components and or their respective oxides that may overlap with the reporter metal isotopes of interest. Additional interface chamber access gates 40 seal off the rest of the device, which remains under vacuum, while the planar sample 10 is being loaded. A primary ion source 50, for example a Cs liquid metal ion gun or an oxygen duo-plasmatron, is focused at the specimen for either modifying the surface by ion milling, material deposition, or for the purpose of imaging the surface.

Once the sample 10 is loaded into the interface chamber 20 and the access gate 30 is closed an interface pump 80 restores the vacuum in the sample interface unit 20 before chamber access gates 40 open and expose the remainder of the device held under vacuum by a separate set of pumps 90, for example turbo-molecular pumps. The ion source 50 serves as a primary ion irradiation unit that irradiates the surface 100 of the sample 10 with primary ions as a primary ion beam 110. The holding unit 60 holds the sample 10. It is desirable that the holding unit 60 have the ability to adjust the X an Y coordinates, with sub-micrometer accuracy, of sample 10 so segments of different locations in the sample can be positioned in the path of the primary ion beam 110 for imaging. The potential gradient generator 70 is disposed in the holding unit 60. Signals applied to deflection controller and amplifier of the primary ion source 50, cause the focused ion beam to move within a target area to be imaged or milled according to a pattern controlled by pattern generator and focusing ion optics 120. Emissions from each sample point may initially be collected by charged particle multiplier 155 to create an image that is displayed on video monitor. An operator viewing the image may adjust the voltages applied to various optical elements in the primary ion source and column 50 to focus the beam and adjust the beam for various aberrations 120. Focusing optics in column 120 may comprise mechanisms known in the art for focusing or methods to be developed in the future. For example, two cylindrically symmetric electrostatic lenses can be implemented to produce a demagnified image of the round virtual source. Because of the low axial energy spread in the extracted beam, chromatic blur is minimal and efficient focusing of the beam can be achieved even at low acceleration voltages (i.e. low beam energies). These properties in conjunction with appropriate focusing optics can be used to generate nanometer, to micrometer scale spot sizes with a range of kinetic energies (0.1 keV-50 keV) and beam currents from a few pico-amperes to several micro-amperes.

The secondary ions 130 that are produced from the segment at the surface of the sample 100 are attracted and focused by the extractor electrodes 140 which oppose the sample 10. The extractor electrodes 140 are disposed so as to oppose a surface of the sample 100 and have the function of collecting secondary ions emitted from the sample 10. The extractor electrodes 140 are disposed between the sample 10 and entrance to the ion transport section 150 of the device so that collected secondary ions can be directed for mass analysis and detection.

Figure 3:
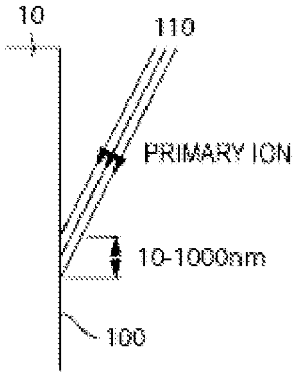
FIG. 3. A schematic diagram representing the incidence of the primary ion beam irradiation on the surface of the planar sample and a description of the desired cross-sectional resolution in accordance with the invention described.

As illustrated in FIGS. 1 and 3, the primary ions emitted from the primary ion source 50 are incident upon the sample surface 100 in an incident axis A direction at an angle Φ in a range from 0 degree (that is, parallel to the surface of the sample 10) to 90 degrees. When primary ions are obliquely incident upon a sample surface 100, collision between the primary ions in the incident axis A direction and the extractor electrodes 140 can be avoided. FIG. 3, exemplifies the incidence and nature of the primary ion beam 110 at the samples surface 100. The aperture of the primary ion source 50, combined with the focusing ion optics/electrode will ensure that abeam 110 with an incident angle of Φ will be able to maintain a cross-section of one micron, or lower e.g., as low as 10 nm).

To ensure the most efficient elemental ionization without multi-atomic adducts and in order to minimize acquisition times, the primary ion beam in the desired embodiment can be a continuous beam of high-energy ions. As used herein, a continuous ion beam may include an ion beam with a duty cycle, as defined by the time the beam was on divided by the sum of the times the beam was on and off, e.g., at least 10%, at least 40%, at least 70%, and up to 100%, although a beam having a duty cycle of at least 1% may be used in circumstances. A primary ion source as described in e.g., *Applied Surface Science,* 255(4):1606-1609, U.S. Pat. No. 8,168,957, U.S. Pat. No. 8,087,379, U.S. Pat. No. 8,076,650, U.S. Pat. No. 7,670,455, and U.S. Pat. No. 7,241,361, which are incorporated by reference herein, using any inert gas or reactive gases such as $O_2$, $N_2$, and $SF_6$ can be used in this embodiment. Thus, suitable primary ion beams may include oxygen, xenon, argon eluding argon cluster), gold (including gold cluster), bismuth gallium, $SF_6$ and $C_{60}$ ion beams. In this specific embodiment, the primary ion source consists of a plasma that is inductively coupled to a compensated RF antenna that can be used in conjunction with focusing optics to produce a high brightness, focused ion beam for SIMS imaging analysis. According to an aspect of the present invention, the RF antenna can be implemented as a helical coil that surrounds a plasma tube. An RF current source is applied to the antenna to induce ionization of the plasma gas in the tube. An impedance matching circuit is provided to allow efficient power transfer to the plasma with appropriate phase shift across the antenna to eliminate plasma potential modulation. The ionized plasma is extracted into an ion beam and focused by ion optics. The ion beam so formed is substantially free of undesirable energy oscillations arising from the RF antenna. Because the RF source imparts only small or ideally no oscillations to the plasma potential, the consequent axial energy spread of the beam arising there from is small. Hence, the ionizing source does not cause substantial chromatic aberration. Moreover, the RF source imparts to the plasma a high ion density.

When coupled with focusing mechanisms, this high-density beam can provide beam currents from a few pico-amperes to current greater than $10^{-11}$, greater than $10^{-10}$ amps, greater than $10^{-9}$ amps, greater than $10^{-8}$ amps, greater than $10^{-7}$ or current of several micro-amperes. A source brightness of at least $10^4$ A/cm$^2$/sr, at least $10^5$ A/cm$^2$/sr, and up to $10^6$ A/cm$^2$/sr or more at 50 keV can be achieved. The axial energy spread is less than 3 eV, less than 2.5 and could be as low as 1.5 eV. The ion beam is capable of being focused into abeam diameter of a few nanometers, up to several tens of micrometers.

The continuous, high brightness primary ion source as described above will be used to produce a continuous emission of secondary ions that will be focused and transferred by the ion transport section 150. This continuous secondary ion current will then be sampled over the entire range of possible masses of interest being analysis by pulsed secondary ion optics and time of flight mass spectrometry. In another embodiment of the invention a high brightness primary ion beam capable of producing elemental secondary ions may also be pulsed (sputtered), in order to release packets of mass ions into the TOF mass analyzer directly.

An electric field that accelerates secondary ions 130 toward the extractor electrodes 140 may be generated by applying a potential Vex, which is appropriate with respect to the potential of the sample 10, to the extractor electrodes 140. Compared to a case in which this electric field is not present, this is advantageous in that efficiency in collecting secondary ions is improved.

The secondary ions emitted from the sample 10 are collected by the extractor electrodes 140, and after that, accelerated up to a predetermined energy due to a potential between the extractor electrodes 140 and the secondary ion transport section 150 so as to transfer the ions efficiently for mass analysis.

Secondary ions from the sample are introduced through a differentially pumped interface 160 into the ion transport section 150 which can comprise an ion deflector 170, apertures 180, an RF ion guide 190 connected to the means of generation of the necessary RF and/or dc voltages 200. The ion deflector 170 can deflect at least a portion of the ions towards the ion guide 190, which can transfer at least some ions through a set of ion optics 210 into the orthogonal accelerator 220, which can comprise a push-out plate 230, grids 240-242 and a set of rings 250. In a usual operation, voltages are applied to the elements that comprise the ion transport section 150 from the appropriate voltage supplies (not shown) in such a manner that a significant portion of the ions of interest are transported into the orthogonal accelerator 220.

At the start of each time-of-flight cycle, a short push-out voltage pulse can be applied to the push-out plate 230, and pull-out voltage pulse may be simultaneously applied to the grid 240; both can be supplied from the pulsing electronics 260. Such pulses can cause ions present between the plate 230 and the first grid 240 to travel sideways through the accelerator 220, towards the right hand grid 242, producing a short in the sideways direction packet of ions that consists predominantly of the ions that were between the plate 220 and the grid 240 at the time of application of the pulses. The ions then can travel through afield-free space 270 towards the ion reflector 295 which can comprise of grids 290 and 300 and rings 305. At least some of the ions can be reflected back and then travel in the field-free space 270 through the grid 310 into the ion detector 320, in which the ions produce electron pulses which can be amplified by an amplifier 330, producing an ion signal waveform corresponding to a single spectrum.

The ions' arrival time at the detector depends on their mass-to-charge ratio, m/z. The ions with the largest m/z arrive at the detector latest. After a time interval sufficient for the latest of the ions of interest to arrive at the detector, the cycle may be initiated again by application of another set of pulses to the plate 230 and the grid 241, which are kept between pulses at voltages appropriate to allow at least some newly delivered by the ion transport section 150 to travel between the plate 230 and the grid 241. Several consecutive such ion signal waveforms that are acquired on several consecutive time-of-flight cycles are shown as 280. Time-of-flight instruments known in the art sample consecutive single spectra completely, for example, by analog-to-digital conversion of complete ion signal waveforms, and transfer digitized data describing such waveforms. In some embodiments, instruments can include means 290 that can sample every ion signal waveform predominantly in a relatively short time window that corresponds to the arrival time of the staining element(s) from a given segment.

For instruments such as that shown in the example, $^{102}$Pd is given as an exemplary staining elemental isotope; however, any other element inherently present or artificially incorporated into the sample 10, can be used. The means 290 sample the single ion spectra predominantly in the time window 11 that corresponds to the arrival time of $^{102}Pd^{+}$. After the signal strength in the time window 11 exceeds a pre-determined detector signal threshold 300, overcoming background signal, the means 290 can start to sample single ion spectra additionally in at least one more time windows 12.

Figure 2:
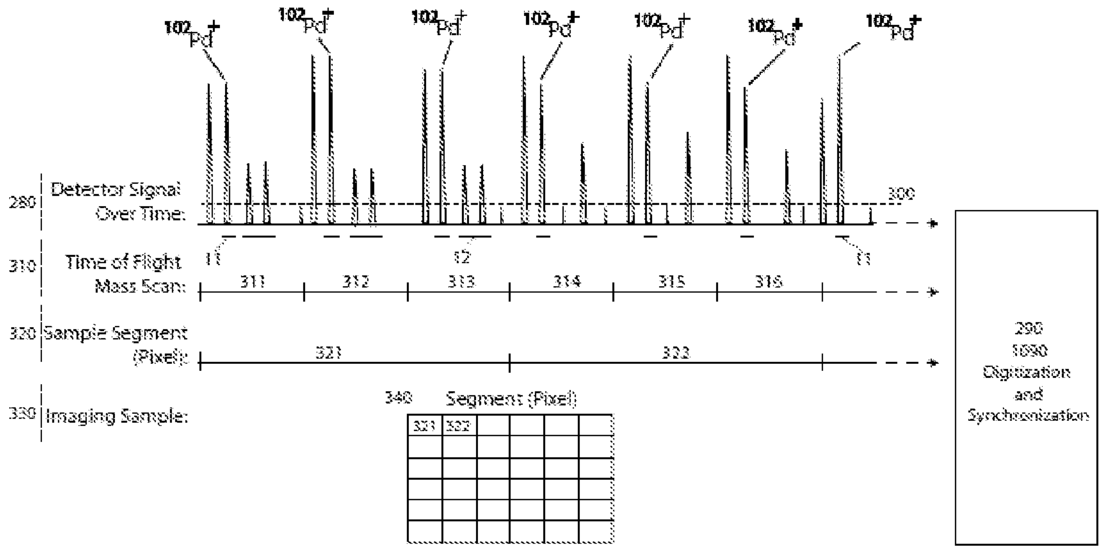
FIG. 2. A schematic representing data digitization and synchronization for reconstruction of atomic mass-encoded images from sequentially analyzed segments of a planar sample.

With the means 290 receiving and recording the TOF-MS detector signal and coordinating it with the timing of the pulsing electronics 260 to create TOF mass information and quantification the synchronizer 1080 coordinates with the means 290, the primary ion source 50, and the sample interface in order to appropriately coordinate the TOF scans 310 with the sample segment 320 currently being ablated by the primary ion beam 110 so as to reconstruct the two dimensional image 330 of mass segment information 340. In the example herein, FIG. 2, the integrated mass information 11, 12, from the detector signal 280, for TOF MS scans 231, 232, 233, would be integrated into single values for each mass channel for sample segment 321. The positional information for segment 321 and its corresponding mass information would be recorded. At the same time, TOF MS scans 314, 315, 316 would be integrated to form the mass information for segment 322. In this example, the irradiation time of the primary ion source on a single segment of the sample would be approximately equivalent to three sequential TOF MS scans. The coordination of this timing, the positional information and the digitization of the integrated mass values would be carried out by the means 290 in coordination with the synchronizer 1080.

In another mode of operation, the instrument is operated with one long sampling window or with a plurality of sampling windows, which correspond to or cover arrival times for ions of all mass-to-charge ratios of interest 311-316. However, only data from the shorter time window 11-12, which corresponds to a primary detection group of mass-to-charge ratio channels, is transferred for further processing. In the event that such data corresponds to the primary ion beam 110 irradiating a particular segment 320, 330 of the sample's surface 100 then data from all of the sampling windows will be transferred for processing and image reconstruction 340 facilitated by the means and a synchronizer of mass and positional information 1090. An advantage of such mode is that the average data transfer rate can be reduced.

In another mode of operation, all data obtained as described in the previous paragraph is transferred; however, only data from the primary mass-to-charge ratio channels is used for processing. Here, processing 290 and synchronization 1090 of the data in the primary mass-to-charge ratio channels can be integrated and recorded for each segment of the sample with its two dimensional position annotated. This will results in a single integrated value for each mass channel for each segment. Thus the average load on the storage of data can be reduced.

Figure 4:
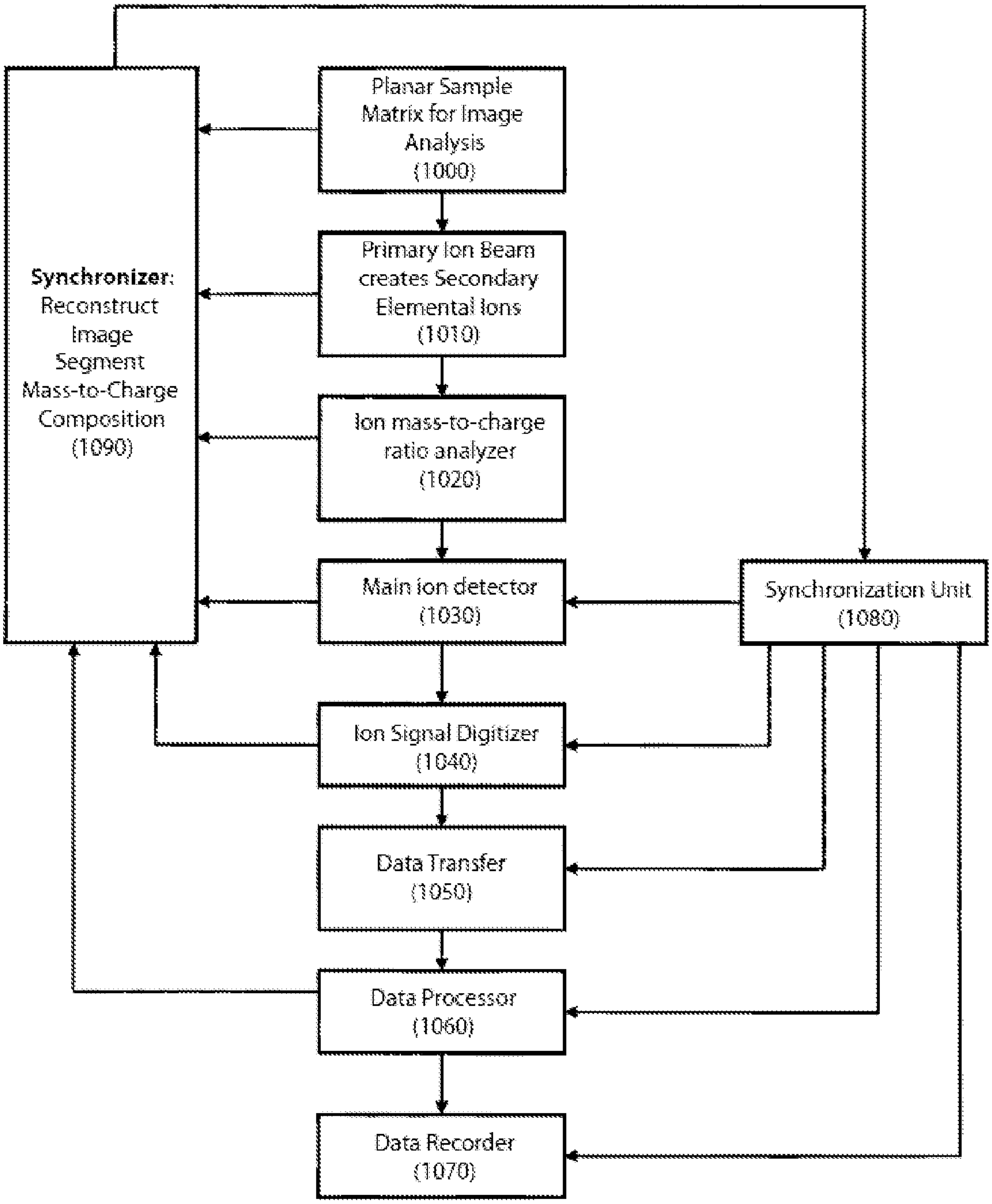
FIG. 4. A workflow schematic illustrating the embodiment of the method and apparatus described.

A flow chart of one embodiment of the method is illustrated in FIG. 4. A sample segment of a planar matrix to be mass imaged by the apparatus 1000 is placed in the analysis chamber. The material associated with the sample segment is vaporized, atomized and ionized by the primary ion irradiation unit 1010, and secondary ions associated with the sample segment are produced. The ions are separated according to their charge-to-mass ratio by the Ion mass-to-charge ratio analyzer 1020, and the main ion detector 1030 detects the separated ions. During times when the primary ion beam 1010 is dwelling on a single segment of the planar sample and image reconstruction is integrating all of the mass measured signals for that segment 1090. During each dwell time the data collected by the main ion detector 1030, digitized by the digitizer 1040, transferred by the digitized data transfer channel 1050, processed by the data processor 1060, is stored by the data recorder 1070. Based on the primary ion source dwell time, all of the ion information measured for each segment can be synchronized and integrated for each mass channel, coordinated by the synchronization unit 1080, so a mass profile for each segment of the planar sample can be reconstructed 1090. The synchronizer 1090 therefore can be used to synchronize one or more other components of the mass spectrometer with the mass information present in a single segment ionized by the primary ion beam.

With reference now to a specific type of embodiment, the detection of ion signals and data processing in Time-of-Flight (TOF) Mass Spectrometry, and in particular methods of operation of a detection system and apparatus for collecting and storing Time-of-Flight Mass-Spectrometry data for analysis of individual particles, is described below.

Time-of-Flight Mass Spectrometers (TOF MS) operate on the principle of measuring the time which ions travel over a fixed distance, the time being usually proportional to the square root of the mass-to-charge ratio of an ion and thus being a measure of the mass of a detected ion. Ions that arrive at an ion detector produce detector output signals that usually consists of a sequence of peaks each representing one or more ions of a particular mass-to-charge ratio (m/z). Generally, the duration of each peak in the mass spectrum is less than 100 nanosecond, and the total duration of the detector output signal which represents ions of all masses usually called single mass spectrum) is of the order of 100 microsecond. Such detector output signals are usually digitized in one of two distinct ways: time-to-digital conversion or transient recording. In a time-to-digital converter (TDC), a counter associated with each arrival time window is incremented when an event of ion arrival is detected within this window. All events of ions arriving at a detector within a certain time period (called "dead time" of the TDC, typically 5-20 ns) can only be counted as one event. As a result, the TDC technique, being an ion counting technique, has been limited by the measurement time dynamic range and is not generally suitable for high dynamic range characterization of rapidly changing ion beams.

One example of a rapidly changing ion beam occurs when a sample segment is ionized and produces an ion cloud that rapidly changes in composition and/or ion density. TOF MS is an example of a preferred method of analysis of ion clouds, in an imaging instrument with a mass spectrometer detector that measures elemental composition of a planar biological sample, specifically for elements that are attached to antibodies or other affinity reagents conjugated to their specific antigens, as described in (Angelo et al. Nature Medicine 2014). The embodied primary ion beam dwell time and duration of produced secondary ion cloud from such a sampling event of 10-10000 microseconds. It is desirable to be able to analyze such a short ion cloud for ions of multiple m/z with dynamic range of at least 4 orders of magnitude.

Another way of digitization of the detector output signal is the use of a transient recorder, in which all of the information in the signal that represents a single TOF mass spectrum (single transient) is captured and stored. For example, transient recorders, based on analog-to-digital converters (ADC), are encountered in commercial Digital Storage Oscilloscopes.

It can be desirable in some circumstances to provide information about the change in elemental composition of a particle-produced ion cloud during transient periods that can last, for example, 10-1000 microseconds. In such circumstances it can be desirable to collect and store multiple mass spectra during such a relatively short period. The duration of a single mass spectrum can desirably be of the order of 10-20 microseconds, allowing 1-1000 spectra to be collected for a single sample segment. A typical width for a single mass window in elemental TOF with a single mass spectrum duration of approximately 20 microsecond is 10-25 nano seconds. A sampling rate of 1 GHz or better can thus be desirable for characterizing ion peak shapes. Such a high sampling rate and $10^4$ dynamic range requirement results in a data generation rate well in excess of 1 GB/s. This is much higher than the fastest data transfer rate (~250 MB/s) achievable with technology known in the art. Recent advances in TOF-MS have made this measurement and data transfer workflow more routine. A TOF analysis data workflow as described in (Bandura Anal Chem 2009 81:6813-22 or U.S. Pat. No. 8,283,624, which are incorporated by reference herein) could be used herein.

In some embodiments, non-elemental secondary ions (e.g., polylatomic secondary species) produced as a result of the primary ion beam impinging upon the sample may be suppressed relative to the secondary elemental atomic ions by energy filtering, thereby enriching for the secondary elemental atomic ions prior to mass separation by the TOF mass spectrometer. Energy filtering may be achieved by any suitable energy filtering means configured to generate an electrostatic sector in the path of the secondary ions and thus deflecting lower energy ions, such as poly-atomic ions, away from the TOF mass spectrometer and allowing the mass spectrum to be derived predominantly from secondary elemental atomic ions with higher energy. Exemplary energy filtering systems are described in, e.g., U.S. Pat. No. 5,166,528; U.S. App. Nos. 20040206899 and 20060284076, which are incorporated by reference herein.

The mass spectroscopy system may comprise: a) a secondary ion mass spectrometry (SIMS) system that comprises a holder for retaining a substrate comprising a sample, wherein the system is configured to (i) scan the sample with a primary ion beam (i.e. oxygen or argon, etc.) and generate a data set that comprises mass-specific abundance measurements of a mass tag that is associated with the sample and (ii) output the data set. In certain cases, the system may further comprise an image analysis module that processes the data set to produce an image of the sample. The holder is in a movable stage that can be controllably moved (e.g., stepped or continuously moved) in at least the x and y directions (which are in the plane of the sample) to facilitate scanning. In a particular embodiment, the system may comprise a continuous beam of primary ions (i.e. a continuous source) linked to a quadrapole, then to an ion pulser, then to a time of flight (TOF) tube.

In some cases, the system comprises: a) a sample interface comprising a holder that is configured to hold a substrate comprising a planar sample; b) a primary ion source capable of irradiating a segment on the planar sample with a beam of primary ions that is less than 1 mm in diameter, wherein irradiation of the planar sample with the primary ions results in the production of secondary elemental atomic ions derived from staining elements associated with the planar sample; and c) an orthogonal ion mass-to-charge ratio analyzer positioned downstream of sample interface, the analyzer being configured to separate secondary elemental atomic ions according to their mass-to-charge ratio by time of flight; d) a main ion detector for detecting the secondary elemental atomic ions and producing mass spectra measurements; and e) a synchronizer, wherein the system is configured so that so that the beam of primary ions scans across the planar sample in two dimensions and the synchronizer associates the mass spectra measurements with positions on the planar sample. As explained above, the system may configured so that the primary ion source continuously irradiates the planar sample as the beam of primary ions scans across the planar sample. As would be apparent, the system may comprise a digitizer for digitizing the output, a data transfer channel for transferring the digitized data output, and other components not described above.

As noted above, the diameter of the beam of primary ions is tunable in that it can changed to a selected diameter, e.g., in the range of 1 mm to 10 nm. In some cases, the primary ion source capable of irradiating a segment of the planar sample of less than 10 um in diameter, less than 1 um in diameter and less than 100 nm in diameter. In these embodiments, the system may be configured to perform an initial "survey" scan from which regions of interest can be identified, and then perform further scans in regions of interest. For example, the mass spectrometer system may be configured to: perform a first scan a first area of the planar sample to collect a first set of data; and perform a second scan the first area of the planar sample to collect a second set of data; wherein the diameter of the beam of primary ions of the first scan is at least 2× larger, at least 5× larger or at least 10× larger than the diameter of the beam of primary ions of the second scan. In these embodiments, the synchronizer associates the mass spectra measurements with a position on the planar sample and the timing of the scans. In some embodiments, the system may be configured to perform a third scan the first area of the planar sample to collect a third set of data, using a beam of primary ions that has a diameter that is smaller (e.g., up to 50% of, up to 20% of or up to 10% of) than the diameter of the beam of the second scan. In some embodiments, the first set of data is collected using a beam of primary ions that has a diameter in the range of 100 μm to 1 mm, or in the range of 100 nm to 100 μm, e.g., 200 nm to 10 μm, and the second set of data is collected using a beam of primary ions that has a diameter in the range of 10 nm to 100 μm, e.g. 10 nm to 10 μm, 10 nm to 3 μm, including 10 nm to 1 μm.

In embodiments in which an area of the planar sample is re-scanned, for a given scan, the primary ion source may sputter off anywhere from 2-10 nm off the top of sample. The upper limit of this range could increase with implementation of the more powerful primary ion sources. The imaging depth for a given field of view is dictated by the total amount of primary ion current per unit area. This dictates how deep the beam penetrates into the sample, which is proportional to the product of the primary ion current and the amount of time each pixel is sputtered (dwell time). Increasing or decreasing the ion current or dwell time will change the depth of penetration into the sample accordingly. In these embodiments, the total signal for a given mass channel should be dictated by the relative abundance of that mass times the total amount of material sputtered (which is dictated by the issues outlined above). So, keeping the primary ion current constant, that means that for mass A which is 100 times more abundant than mass B, a pixel dwell time t/100 for A should generate the same amount of signal as a dwell time oft for B.

Survey scans using highly abundant markers, e.g., cytochemical or IHC, can use short pixel dwell times. For example, the signal for hematoxylin is up to 1E3 more intense than many IHC markers, such that a survey scan could be acquired with very short pixel dwell times. This has the advantage of not only getting the image quickly, but because the dwell times are very short, the sputter depth is very shallow and little of the sample surface is consumed, leaving essentially all of the IHC markers intact for subsequent scans. Survey scans can also be performed by using larger pixel sizes. To the extent that the current density is constant, the gain in speed that can be achieved by varying the beam diameter (D) is proportional to D^2, so, an image at 1 um beam spot size can be acquired 16× faster than one at 250 nm beam spot size.

In some embodiments, the system may configured to move the planar sample to a defined position, thereby presenting a first area on planar sample to the beam of primary ions and raster the beam of primary across the first area to produce a plurality of mass spectra measurements for the first area. In these embodiments, the first area may be in the range of 0.1 mm×0.1 mm to 1 mm×0.1 mm, e.g., about 0.5 mm×0.5 mm. In these embodiments, the system may be additionally configured to: c) move the planar sample to a second defined position after the plurality of mass spectra measurements for the first area have been collected, thereby presenting a second area on the planar sample to the beam of primary ions; and d) raster the beam of primary across the second area to produce a plurality of mass spectra measurements for the second area. A substantial part of an region of interest on a planar sample can be scanned in this manner, i.e., by first moving the substrate to so that a selected area in a region of interest is in the field of view for the beam, and then rastering the beam through the area.

Due to the resolution of elemental analysis and the number of elemental isotopes that can be used, it is possible to simultaneously measure up to 100 or more parameters within a single segment (pixel) without experiencing spectral/signal overlap. As discussed above, the mass spectrometer system to can be used to independently measure the abundance and positions of multiple mass tags in a planar sample of biological material. In these embodiments, the data output may contain the abundance and position of several mass tags (e.g., more than 2 mass tags, up to 5 mass tags, up to 10 mass tags, up to 20 mass tags, up to 50 mass tags, up to 100 mass tags, up to 200 or more mass tags). The image analysis module may combine data sets obtained from multiple scanned areas into a single data set, wherein each of the multiple scanned areas are offset from one another. The image analysis module may adjust the offset between adjacent scanned areas so as to increase the overlap of pixels with similar mass tag intensities near the edges of the adjacent scanned areas.

In some embodiments, an image at least part of the planar sample may be constructed by placing the planar sample comprising staining elements into the holder of the mass spectrometer system described above; and producing a data file containing mass spectra measurements for an area of the planar sample using the mass spectrometer system, wherein the mass spectra measurements are associated with positions on the planar sample; and reconstructing an image of the of the planar sample using the mass spectra measurements. A datafile of the image (e.g., a pdf or gif) may be forwarded to a remote location. In some embodiments, the image may displayed on a screen.

The image analysis module may transform the data set into one or more false color images (e.g. pseudocolor, pseudo-brightfield, pseudo-immunofluorescence). The image may be in any suitable image file format (e.g., JPEG, Exif, TIFF, GIF, PNG, a format readable by an image analysis software such as ImageJ, and so forth). In certain embodiments, the image analysis module may produce the image by transforming the abundance (e.g., measured intensity) of one or mass tags into the intensity of one or more false colors at individual pixels in the image. The relationship between the intensity of a mass tag and the intensity of the corresponding false color may be linear or non-linear (e.g., logarithmic, exponential, etc.).

In certain embodiments, the system is configured to generate a multiplexed data set comprising spatially-addressable measurements of the abundances of a plurality of mass tags that are bound to an area on the surface of the sample. The image analysis module may transform the plurality of mass tag measurements to produce a plurality of false color images. The image analysis module may overlay the plurality of false color images (e.g., superimpose the false colors at each pixel) to obtain a multiplexed false color image. Multiple mass tag measurements (e.g., unweighted or weighted) may be transformed into a single false color, e.g., so as to represent a biological feature of interest characterized by the binding of the specific binding reagent associated with each of the multiple mass tags. False colors may be assigned to mass tags or combinations of mass tags, based on manual input from the user. Alternatively or in addition, an unsupervised approach may be used to determine groups of mass tags to be represented by a single false color. The unsupervised approach may identify groups of mass tags that maximizing variance while minimizing the number of groups (e.g., such as through principle component analysis (PCA)), grouping mass tags that are co-localized and/or in proximity (e.g., by any suitable clustering algorithm), or may employ any other suitable method for grouping mass tags to be represented by a single false color. In certain aspects, the image may comprise false colors relating only to the intensities of mass tags associated with a feature of interest, such as mass tags in the nuclear compartment.

The image analysis module may further be configured to adjust (e.g., normalize) the intensity and/or contrast of mass tag intensities or false colors, to perform a convolution operation (such as blurring or sharpening of the mass tag intensities or false colors), or perform any other suitable operations to enhance the image. In certain aspects, the image analysis module may compile data sets generated from multiple 2D scans to produce an image that is a 3D model of the cells. The image analysis module may perform any of the above operations to align pixels obtained from successive 2D scans and/or to blur or smooth mass tag intensities or false colors across pixels obtained from successive 2D scans to produce the 3D model.

In certain embodiments, the method may comprise: performing a survey scan of the planar sample to identify regions of interest; and re-scanning the regions of interest: by rastering the ion beam at a higher resolution than the survey scan; using a beam of primary ions having a smaller diameter than the survey scan; with a longer segment acquisition time than the survey scan, thereby collecting more mass spectra per segment or spectra from more ions per segment or with a larger mass range than the survey scan, thereby measuring a greater number of elemental isotopic masses per segment. In this method, the region of interest are computationally or manually identified in the initial survey scan; and/or areas of the planar substrate that are found to be devoid of sample are omitted from subsequent imaging analyses.

In these embodiments, the visual image of the planar sample may be reconstructed with color or shading scales based on individual or combined levels of mass-to-charge species.

The image analysis method may be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive), etc.

What is claimed is:

1. A mass spectrometer system for elemental analysis of a planar sample, the mass spectrometer system comprising:

a) a sample interface comprising a holder that is configured to hold a substrate comprising a planar sample;

b) a primary ion source capable of irradiating a segment on the planar sample with a beam of primary ions that is less than 1 mm in diameter, wherein irradiation of the planar sample with the primary ions results in the production of secondary elemental atomic ions derived from staining elements associated with the planar sample;

c) an orthogonal ion mass-to-charge ratio analyzer positioned downstream of sample interface, the analyzer being configured to separate secondary elemental atomic ions according to their mass-to-charge ratio by time of flight;

d) a main ion detector for detecting the secondary elemental atomic ions and producing mass spectra measurements; and e) a synchronizer that associates the mass spectra measurements with positions on the planar sample, wherein the system is configured so that so that the beam of primary ions scans across the planar sample in two dimensions.

2. The mass spectrometer system of claim 1, wherein the system is configured so that the primary ion source continuously irradiates the planar sample as the beam of primary ions scans across the planar sample.

3. The mass spectrometer system of claim 1, wherein the diameter of the beam of primary ions is tunable to a selected diameter in the range of 10 nm to □ mm.

4. The mass spectrometer system of claim 1, wherein the system is configured to:

perform a first scan a first area of said planar sample to collect a first set of data; and perform a second scan said first area of said planar sample to collect a second set of data;

wherein the diameter of the beam of primary ions of the first scan is at least 2× larger than the diameter of the beam of primary ions of the second scan, and the synchronizer associates the mass spectra measurements with a position on the planar sample and the timing of the scans.

5. The mass spectrometer system of claim 4, wherein the system is configured to perform a third scan the first area of said planar sample to collect a third set of data, using a beam of primary ions that has a diameter that is smaller than the diameter of the beam of the second scan.

6. The mass spectrometer system of claim 4, wherein the first set of data is collected using a beam of primary ions that has a diameter in the range of 100 nm to 100 μm and the second set of data is collected using a beam of primary ions that has a diameter in the range of 10 nm to 1 μm.

7. The mass spectrometer system of claim 1, wherein the system is configured to:

a) move the planar sample to a defined position, thereby presenting a first area on planar sample to the beam of primary ions and b) raster the beam of primary across said first area to produce a plurality of mass spectra measurements for said first area.

8. The mass spectrometer system of claim 7, wherein the system is configured to:

c) move the planar sample to a second defined position after said plurality of mass spectra measurements for said first area have been collected, thereby presenting a second area on the planar sample to the beam of primary ions; and d) raster the beam of primary across said second area to produce a plurality of mass spectra measurements for said second area.

9. The spectrometer system of claim 8, further comprising repeating steps c) and d) until sufficient data has been collected.

10. The mass spectrometer system of claim 1, wherein the planar sample is mounted on a conductive substrate where the substrate surface has been depleted of atoms that give rise to said secondary elemental atomic ions.

11. The mass spectrometer system of claim 1, wherein said beam of primary ions ionize mass tags in the planar sample, and said mass spectra measurements comprise the abundance and identify of said mass tags.

12. The mass spectrometer system of claim 1, wherein said beam of primary ions is an oxygen, xenon, argon, gold, bismuth gallium, $SF_6$ or $C_{60}$ ion beam.

13. The mass spectrometer system of claim 1, wherein said mass tags comprise elements having an atomic number of 21-29, 39-47, 57-79 or 89.

14. The mass spectrometer system of claim 1, wherein the system comprises an energy filtering means configured to enrich for the secondary elemental atomic ions before they are separated by the analyzer.

15. A method for reconstructing an image of a planar sample, comprising:

(a) placing said planar sample comprising staining elements into the holder of the mass spectrometer system comprising:

i. a sample interface comprising a holder that is configured to hold a substrate comprising a planar sample;

ii. a primary ion source capable of irradiating a segment on the planar sample with a beam of primary ions that is less than 1 mm in diameter, wherein irradiation of the planar sample with the primary ions results in the production of secondary elemental atomic ions derived from staining elements associated with the planar sample;

iii. an orthogonal ion mass-to-charge ratio analyzer positioned downstream of sample interface, the analyzer being configured to separate secondary elemental atomic ions according to their mass-to-charge ratio by time of flight;

iv. a main ion detector for detecting the secondary elemental atomic ions and producing mass spectra measurements; and v. a synchronizer that associates the mass spectra measurements with positions on the planar sample, wherein the system is configured so that so that the beam of primary ions scans across the planar sample in two dimensions;

(b) producing a data file containing mass spectra measurements for an area of the planar sample using the mass spectrometer system, wherein said mass spectra measurements are associated with positions on the planar sample; and (c) reconstructing an image of said of the planar sample using the mass spectra measurements.

16. The method of claim 15, further comprising sending said data file and/or the image to a remote location.

17. The method of claim 15, wherein the method comprises:

performing a survey scan of the planar sample to identify regions of interest; and re-scanning the regions of interest:

i) by rastering said ion beam at a higher resolution than the survey scan;

ii) using a beam of primary ions having a smaller diameter than the survey scan;

iii) with a longer segment acquisition time than the survey scan, thereby collecting more mass spectra per segment or spectra from more ions per segment iv) with a larger mass range than the survey scan, thereby measuring a greater number of elemental isotopic masses per segment.

18. The method of claim 17, wherein the region of interest are computationally or manually identified in the initial survey scan; and areas of the planar substrate that are found to be devoid of sample are omitted from subsequent imaging analyses.

19. The method of claim 15, wherein the visual image of the planar sample is reconstructed with color or shading scales based on individual or combined levels of mass-to-charge species.

20. The method of claim 15, wherein the image is displayed on a screen or an electronic file of the image with mass-to-charge information is produced.

* * * * *